United States Patent [19]

Dupoy De Guitard et al.

[11] Patent Number: 5,122,374

[45] Date of Patent: Jun. 16, 1992

[54] **PHARMACEUTICAL PRODUCT HAVING EPIDERMAL REGENERATIVE ACTIVITY BASED ON THE ACTIVE INGREDIENT OF *MIMOSA TENUIFLORA* AND PROCESS FOR ITS OBTENTION**

[76] Inventors: Jacques Dupoy De Guitard, Isaac Peral, 46, Madrid, Spain, 28040; Julio Téllez Pérez, Taller Retorno, 12 No. 9, Mexico City, Mexico

[21] Appl. No.: 367,708

[22] Filed: Jun. 19, 1989

[30] Foreign Application Priority Data

Jun. 28, 1988 [ES] Spain .................................. 8802029

[51] Int. Cl.$^5$ ............................................. A61K 35/78
[52] U.S. Cl. ................................................... 424/195.1
[58] Field of Search ...................................... 424/195.1

[56] References Cited

U.S. PATENT DOCUMENTS 121,631 12/1871 Kennedy ......................... 424/195.1
4,883,663 11/1989 Leon et al. ...................... 424/195.1

OTHER PUBLICATIONS

Remington, Practice of Pharmacy, 1895 pp. 438–443.

*Primary Examiner*—John W. Rollins
*Assistant Examiner*—Ralph Gitomer
*Attorney, Agent, or Firm*—Wenderoth, Lind & Ponack

[57] ABSTRACT

There is provided a method for producing an active ingredient isolated from the cortex of *Mimosa tenuiflora* by solvent extraction. The active ingredient has epidermal regenerative properties such as utility in the treatment of burns.

4 Claims, 4 Drawing Sheets

PHARMACEUTICAL PRODUCT HAVING EPIDERMAL REGENERATIVE ACTIVITY BASED ON THE ACTIVE INGREDIENT OF *MIMOSA TENUIFLORA* AND PROCESS FOR ITS OBTENTION

SUMMARY

The cortex of *Mimosa tenuiflora* contains a compound which possesses regenerative properties which compound, once extracted, yields an odourless, reddish coffee-coloured powder having a bitter taste, the structural analysis of which presents a content in C of 54–57%, in H of 4.5–5.4% and in O from 36.5 to 37.5%.

The obtention process essentially consists in extracting, by means of solvents, the active ingredient contained in the *Mimosa tenuiflora* cortex previously ground. The preferred solvents used are chloroform, ethanol and water. The process is conducted at moderately high temperatures.

The thusly obtained active ingredient is useful in the therapy of burns, chafings, grazes, sores, eczemas, slight wounds and surgical wounds and may be administred in a solid or liquid form. The aqueous solutions of the said active ingredient as well as the dustable powders are preferred.

1. Field of the Invention

The present invention refers to a process for extracting and isolating an active ingredient contained in the cortex of the *Mimosa tenuiflora* tree; to the so obtained active ingredient having epidermal regenerative properties and to the pharmaceutical compositions containing the said active ingredient. The preparation of the said pharmaceutical compositions is another object of the invention.

The said active ingredient contains a potent epidermal regenerative inducing factor and it is particularly suitable for and effective in the treatment of burns, ulcers, varicose veins, surgical wounds, slight wounds, cracks, scratches, grazes, sores and eczemas, and it is furthermore a pilose follicle stimulant.

2. State of the Art

The active ingredient of this invention has not as yet been completely identified insofar as its structure.

The utilisation of the cortex of the *Mimosa tenuiflora* tree, known as TEPESCOHUITE, dates from the prehispanic Mexican times to our days. The historic background thereof goes back to the use by the Mayan indians in the southern part of the country, a place from where the said plant is a natural.

It was described for the first time by Mr. Francisco Hernandez in his book entitled "History of the Plants of New Spain" during the XVII century, when he acted as Philip II's Protodoctor. During his stay in New Spain, he devoted his time to compiling and codifying the knowledge of Medicinal Botany.

It appears in his book in the Nahuatl language under the name of TETLATILIZTLI and it was widely known in the Mexican valley by the ancient Mexicans or Aztecans.

The natives of the region of the Cintalapa valley, Chiapas and other regions have been using the cortex of the adult trees merely in a ground form, and sterilisation thereof consisted in roasting it in a pan and then dusting it on the burn.

Currently the cortex of the *Mimosa tenuiflora* tree is still being used in a rudimentary manner by dusting the powder resulting from the grinding of the cortex on the wound. This neither permits a suitable exploitation of the properties of the active ingredients nor the adequate dosage thereof, for which reason doctors are reluctant to use this curative method.

Further the number of persons afflicted with burns has been increasing in the majority of industrialised countries and in countries under development, due to the demographic accumulation in the large cities and to the increase in the birth rate.

A statistical study carried out recently in 1980 in the United States of America, by the World Organization of Health and by the U.S. Public Health Department, showed that one out of every 10 persons who had some kind of accident and were admitted to a medical centre, is related to some kind of trauma due to burns. And that from about 200,000 to 300,000 of these burned persons necessitate a prolonged convalescence, more than one month, as well as an orthopaedic rehabilitation stage which varies of from some weeks to months, and that about 10,000 to 12,000 of these patients died during 1980.

The treatment in any developed country of a person, 50% of whose body surface has been burned and who is suffering from a perdominantly second degree injury, superficial or deep, is very costly, since the daily hospitalization costs oscillates between 300 and 1,000 U.S. dollars.

Due to the complications involved in the therapies because of the use of different types of grafts and the prolonged hospitalization time, a conservative estimation would be of about 36,000 U.S. dollars.

Furthermore, the therapies used are not simple because of the deffinient health infrastructure in other countries in which not all the patients receive the same quality of medical attention; all this, combined with the prolonged treatment time which these patients require, makes hospitalization expensive.

This problem would be solved in part by using the active product of the invention which, since it enables the properties of the *Mimosa tenuiflora* cortex to be fully exploited, and by means of a highly simple application, would reduce intrahospitalization of the patient in about 50%.

Therefore, the need arises for investigating and updating a suitable methodology for extracting, isolating and characterising the fraction of the active ingredient contained in the *Mimosa tenuiflora* cortex, and once isolated from the other non-active components, prepare, by means of the suitable excipients and carriers, medicaments capable of being suitably applied and the dosage of which may be controlled. This is precisely one of the objects of the present invention.

DESCRIPTION OF THE INVENTION

1. Object of the Invention

A first object of the invention is the active ingredient having epidermal regenerative properties contained in the *Mimosa tenuiflora* cortex, and the pharmaceutical compositions prepared on the basis of the said active ingredient.

A second object of the invention is to provide a process for extracting and isolating the said active ingredient.

2. Description of the Drawings

DETAILED DESCRIPTION OF THE INVENTION

The active ingredient having epidermal regenerative properties contained in the *Mimosa tenuiflora* cortex and obtained in accordance with the extracting process which will later on be described, presents the following characteristics:

a) Physical characteristics:

a.1. Organoleptic characteristics: This compound is an odourless, reddish coffee-coloured powder, having a bitter taste.

a.2. Melting point: This was caluclated with a Fisher-Johns apparatus. The active compound presents a melting point of 222° C.

a.3. Solubility: This study was conducted with solvents having different polarities at ambient temperature.

| Solvent | mg/ml |
|---|---|
| Ethanol | 93 |
| Dimethylsulfoxide | 224 |
| Methanol | 175 |
| Acetone | 16 |
| Water | 0 |
| Chloroform | 0 |
| Ethyl acetate | 0 |
| Ethyl ether | 0 |
| Propanol | 0 |
| Hexane | 0 |
| Carbon tetrachloride | 0 |
| Tetrahydrofurane | 0 |
| Petrolate | 0 |
| Dioxane | 0 |
| Amyl alcohol | 0 |
| Isopropyl alcohol | 0 |
| Benzyl alcohol | 0 |
| Diethyl amine | 0 | a.4. Purity tests: Thin layer chromatography was used, utilizing Merck DC-Alufolien Kieselgel 60 chromatopapers having a thickness of 0.2 mm. and employing the following eluting systems:

| Solvents | RF |
|---|---|
| a). Chloroform | 0 |
| b). Ethyl acetate | 0 |
| c). Petroleum ether | 0 |
| d). Benzene | 0 |
| e). Methanol-water-DMSO 1:1:1: v/v | 0.963 |
| f). Ethanol-water-acetic acid 2:1:1 v/v | 0.817 |
| g). Methanol-dimethylsulfoxide | 0.910 |
| h). DMSO | 1,000 |
| i). Dioxane-methanol-ethyl acetate 1:1:1 V/V | 0 | a.5. Heavy metal content: Analysis was carried out in an Atomic Absorption spectrophotometer, (Perkin-Elmer model 5000), obtaining the following results (in parts per million):

| Element | Concentration ppm |
|---|---|
| Pb | 0 |
| Zn | 0 |
| Cr | 0 |

| Element | Concentration ppm |
|---|---|
| Fe | 0 |
| Mn | 0 |
| Cu | 0 |
| Hg | 0 |
| As | 0 | a.6. Absolute humidity: This was calculated on the basis of the constant weight technique, employing for this test, one gramme of the active ingredient. The humidity obtained was of 10.01%.

a.7. Ignition residues: The residue obtained after burning one gramme of active ingredient was of 885 mg of ash.

a.8. pH of the solution: Different concentrations of active ingredient were prepared in an aqueous solution. The readings were taken in a potentiometer (Conductronic pH 10), at a temperature of 25° C. The results obtained are shown below:

| Concentration (mg/ml) | pH |
|---|---|
| 100 | 3.94 |
| 177 | 3.11 |
| 316 | 3.09 |
| 562 | 3.08 |
| 1000 | It does not dissolve | b) Spectral characteristics:

b.1.

Figure 1:
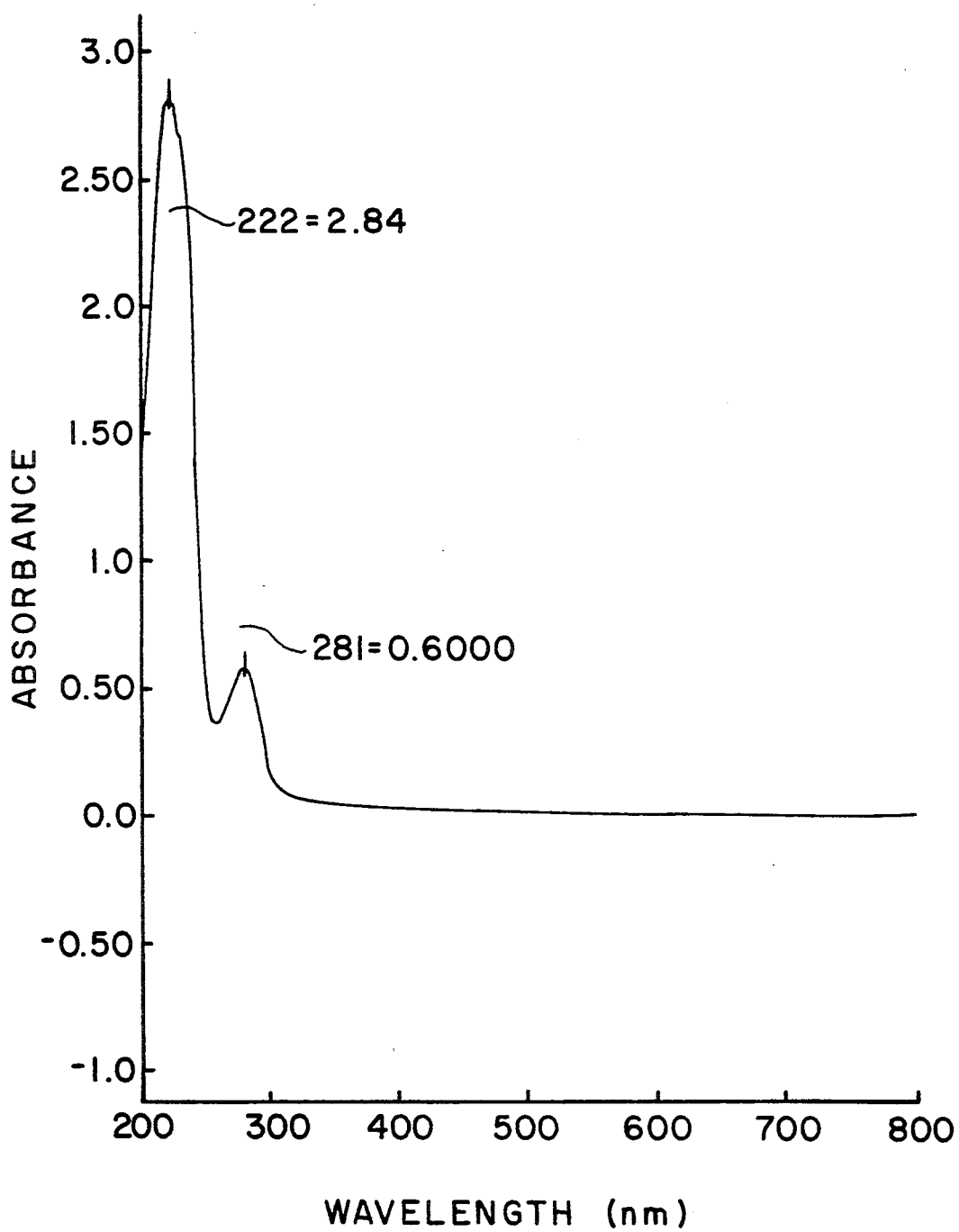
FIG. 1 illustrates a UV-VIS absorption spectrum of the active ingredient extracted from the *Mimosa tenuiflora* cortex.

Ultraviolet absorption spectrum: See FIG. 1.
Instrument: UV-VIS specord
Solvent: Ethanol

| λmax (nm) | absorbence |
|---|---|
| 222 | 2,840 |
| 281 | 0,600 | b.2.

Figure 2:
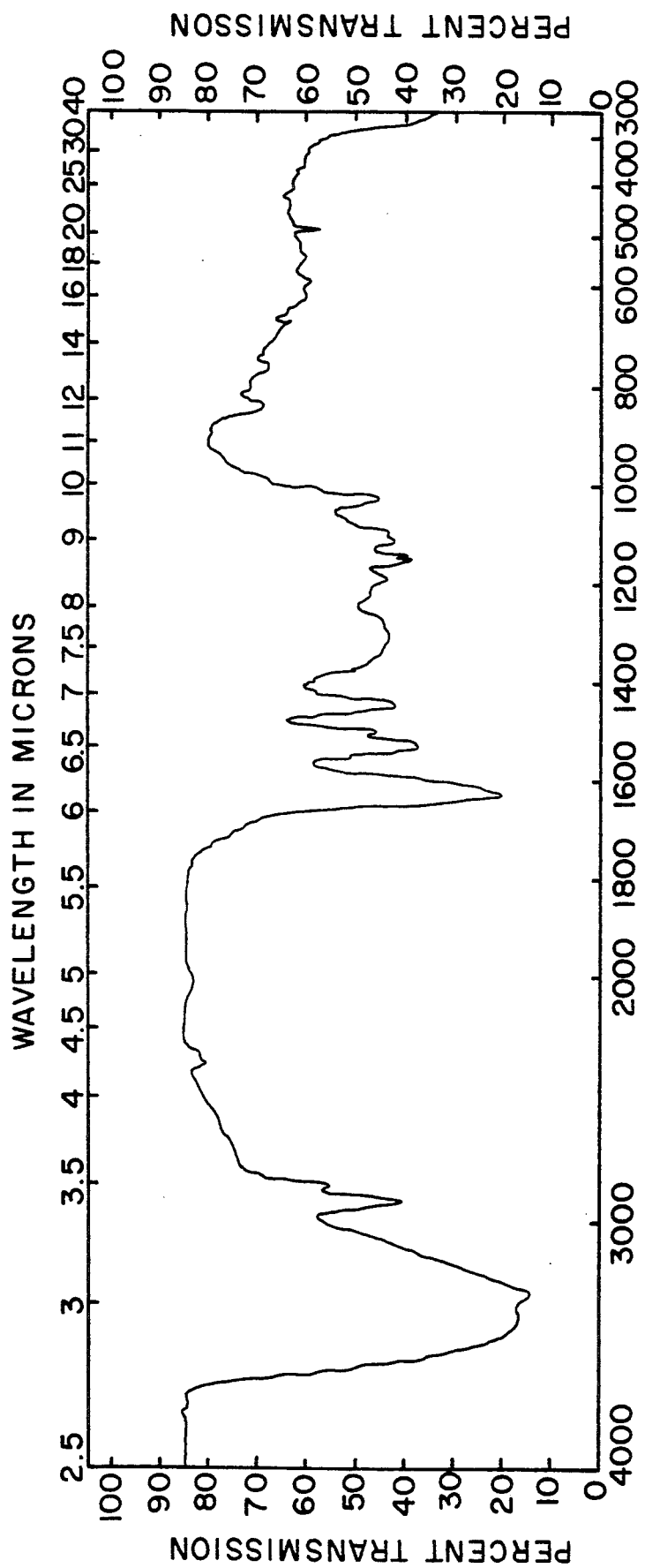
FIG. 2 illustrates the infrared absorption spectrum of the said active ingredient.

Infrared absorption spectrum: See FIG. 2
Instrument: IR 75 specord In potassium bromide tablet.

Main absorption bands: 3290, 2910, 1630, 1530, 1450, 1190, 1150, 1110, 1020, 840, 760, 620, 580 cm$^{-1}$.

b.3.

Figure 3:
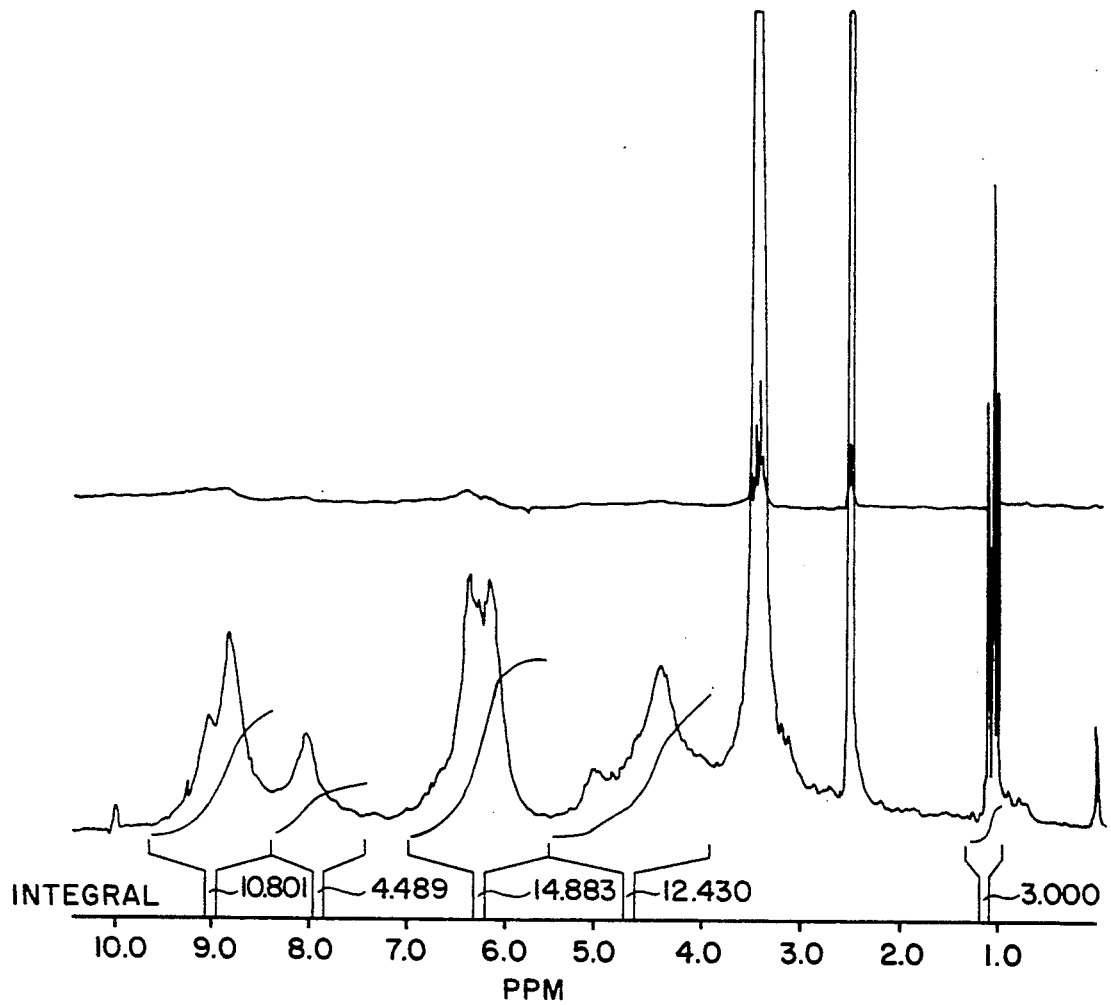
FIG. 3 illustrates the proton magnetic resonance spectrum of the said active ingredient in $D_2O$.

Proton magnetic resonance spectrum: See FIG. 3.
Instrument: Bruker HX-90 E, with DMSO as the reference pattern.
Solvent: $D_2O$.

NMR $^1H$ δ (ppm): 1.13 (multiplet); 3.36 (m); 4.33 (singlet); 5.1 (s); 6.24 (doublet); 8.01 (s); 8.81 (s); 9.01 (s); 9.98 (s).

b.4.

Figure 4:
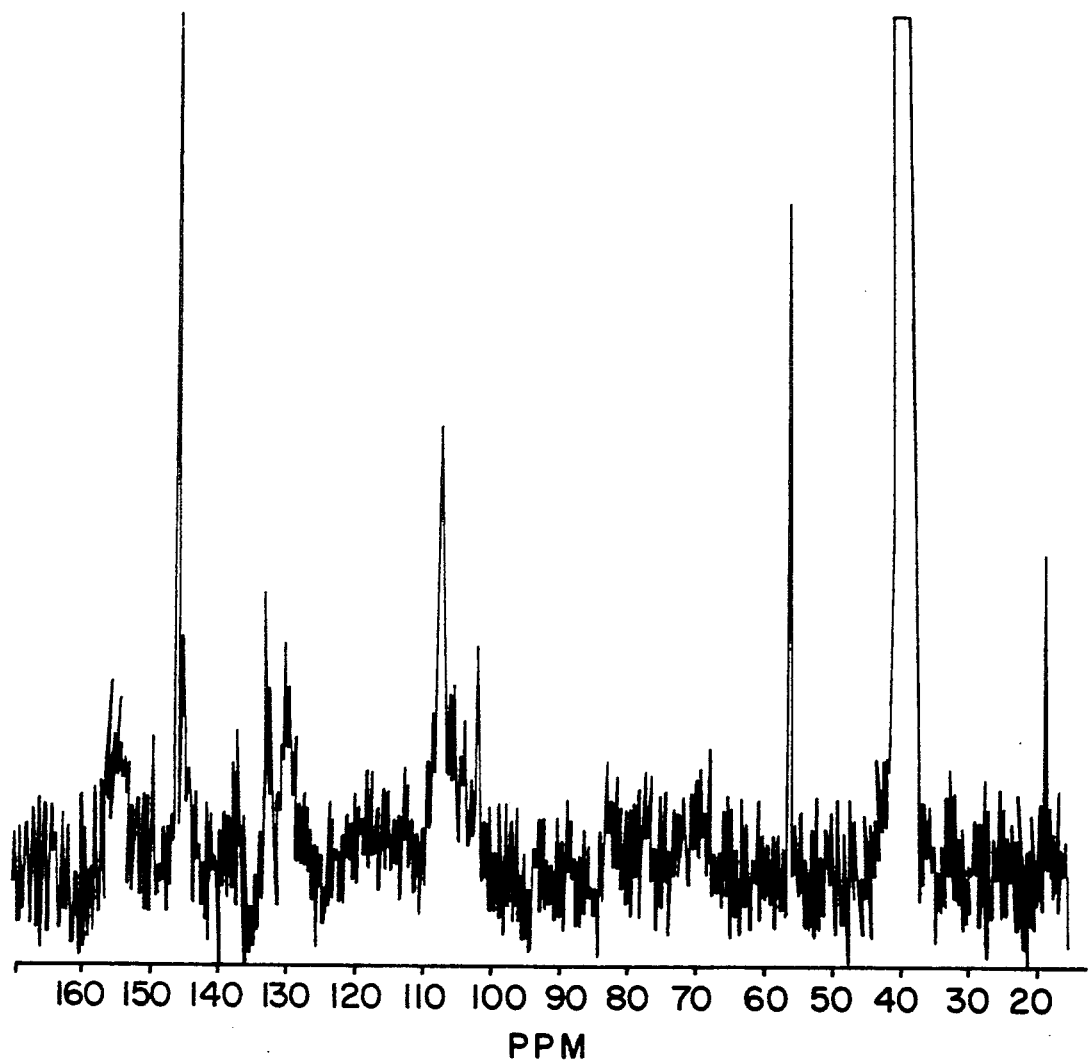
FIG. 4 illustrates the $^{13}C$ magnetic resonance spectrum of the said active ingredient in $D_2O$.

$^{13}C$ magnetic resonance spectrum: See FIG. 4
Instrument: Bruker HX-90 E with TMS as the reference pattern.
Solvent: $D_2O$.

NMR $^{13}C$ δ (ppm) 17.5, 18.25, 18.57, 19.5, 20.02, 21, 23, 25, 25.5, 26.25, 27.5, 27.9, 32, 32.8, 33.56, 36.4, 36.52, 37.5, 42, 42.2, 43, 45.2, 47.2, 49.2, 50.2, 52, 54, 55, 59.5, 60, 60.2, 62,7, 64.7, 65, 67.2, 68, 68.1, 69, 69.9, 70.5, 71.7, 74.2, 75, 76, 76.5, 77, 78.2, 81.2, 82.5, 83, 89, 96, 98, 98.7, 100, 102, 103.2, 103.5, 105, 105.2, 105.5, 106.5, 107.5, 109.7, 112, 112.2, 112.5, 112.7, 115, 115.7, 117.5, 118.5, 119.7, 123.5, 127, 128, 128.8, 129, 130, 131.5, 132 136.9, 137.5, 143, 144.2, 144.7, 144.5, 146.2, 149.5, 150.5, 151, 152.7, 153.5, 153.6, 153.7, 155.5, 156, 157, 158, 160, 164, 163, 166, 167. ONLY UP TO 170 WAS READ.

c) Chemical characteristics:

c.1. Elemental anaylysis: C: 54-57%, H: 4.5-5.4%, O: 36.5-37.5%.

c.2. Chemical reactions:

| A) Reagent | Result |
| --- | --- |
| 1% Ferric chloride | Greenish coffee colour |
| 1% Lead acetate | White precipitate |
| Bromine water | It produces decolorisation |
| Picric acid | Straw yellow colour |
| Ninhydrin | Negative |
| Fluoroglucitol | Negative |

B) Acid hydrolysis with sulphuric acid

A solution of 250 mg of the active ingredient in 10 ml of 2N sulphuric acid were placed in a glass phial, it was sealed and heated in a bainmarie for 1.5 hours. The hydrolysis products were separated by dry column chromatography using a 70-230 mesh silica gel support (Merck). The eluant used was CCl-ethyl acetate-Ethanol (4:2:1 v/v) and the following fractions were obtained from below upwards:

1. Pink colour
2. Yellow colour
3. Dark red colour
4. Light red colour
5. Dark red colour which presented the following physical characteristics:
Melting point above 300° C.
Soluble in ethanol, DMSO, acetone, methanol
Insoluble in Cl$_4$C, benzene, ethyl acetate.

The spectroscopic study of the fractions obtained was then carried out. The IR spectrum was run in KBr, and deuterated DMSO was used for the NMR determination. The results obtained were:

Fraction 1

IR, absorption bands: 3380, 2900, 1630, 1520, 1380, 1220, 1060, 1010, 920, 780, 620, 580, 480, 430 cm$^{-1}$.

NMR $^1$H: 1,042 (t), 3.44 (quadruplet), 3.76 (d), 5.02 (s), ppm.

Fraction 2

IR, absorption bands: 3290, 2910, 1630, 1530, 1440, 1210, 1110, 1030, 760 cm$^{-1}$.

NMR $^1$H: 1.22 (s), 3.30 (s), 6.5 (m), 8.78 (m), ppm.

Fraction 3

IR, absorption bands: 3290, 2910, 1620, 1520, 1430, 1360, 1000, 760 cm$^{-1}$.

NMR $^1$H: 0.85 (s), 1.10 (s), 1.22 (s), 3.15 (s), 3.40 (s), 3.70 (s), 4.13 (s), 4.56 (s), 7.68 (s), 7.83 (s) ppm.

Fraction 4

IR, absorption bands: 3290, 2980, 1710, 1540, 1470, 1450, 1430, 1330, 1230, 1110, 1070, 1020, 940, 800, 620, 580, 490, 430 cm$^{-1}$.

Fraction 5

IR, absorption bands: 3290, 2920, 1610, 1520, 1440, 1190, 1110, 1020, 830, 660, 650 cm$^{-1}$.

These fractions were then derivatized to obtain the corresponding acetates. For such purpose, 100 mg. of each fraction were taken, with the exception of fraction 3 since the amount obtained from the acid hydrolysis was minimum. They were dissolved in DMSO and 3 ml of acetic anhydride and 1.5 ml of pyridine were added. It was allowed to stand for five days, after which 5 ml of distilled water were added. It was dried under reduced pressure and the residue obtained was dissolved in DMSO and dry column chromatographed using a 70-230 mesh silica gel support (Merck). The following systems were used as eluants:

a) For the acetate of the first fraction: acetone-chloroform 2:1 v/v b) For the acetates of fractions 2, 4 and 5: chloroform-methanol 3:2 v/v Spectroscopic study. The IR run in KBr was taken of the acetylated compounds. For the NMR determination, deuterated DMSO was used.

Fraction 1

NMR $^1$H (DMSO as a reference): 1.3(t), 1.94(s), 2.03(s), 3.4(d), 3.43(s), 3.69(m), 8.1(m), 8.59(t), 8.93(s) ppm.

NMR $^{13}$C: 15.27, 18.68, 20.7, 56.2, 61.7, 127.5, 142.3, 146.6 ppm.

NMR (with chloroform as the reference): 0.9(s), 1.3(s), 1.6(s), 2.0(s), 2.2(s), 2.35(t), 2.55(s), 7.5(m), 7.63(m) ppm.

Fraction 2

NMR $^1$H (DMSO as the reference): 1.15(d), 1.20(s), 1.9(s), 2.06(s), ppm.

Fraction 5

NMR $^1$H (DMSO as the reference): 1.12(m), 2.02(m), ppm.

c) Acid hydrolysis with 2N periodic acid

A solution of 1 g. of the active ingredient in 50 ml. of 2N periodic acid was subjected to reflux temperature for 1.5 hours. The hydrolysis products were separated by dry column chromatography using a 70-230 mesh silica gel support (Merck). The following systems were used as eluants:

a) Chloroform-methanol 3:2 v/v b) Carbon tetrachloride-ethyl acetate-ethanol 4:2:1 v/v.

The following fractions were obtained from below upwards:

COLOUR:
1. Violet
2. Strong yellow
3. Straw yellow
4. Pale coffee
5. Dark coffee Spectroscopic study. The IR run in KBr was taken of the compounds obtained. For the NMR determination deuterated DMSO was used.

Fraction 1

NMR $^1$H (DMSO as the reference): 0.93 (m), 1.22 (s), 2.09 (s), ppm.

Fraction 2 (chloroform as the reference)

IR, absorption bands: 2922, 2820, 1727, 1702, 1625, 1933, 1384, 1130, 1064 cm$^{-1}$.

NMR $^1$H: 0.83 (s), 1.035 (t), 1.22 (s), 3.35 (s), 3.48 (s), 3.63 (s), ppm.

Fraction 3

IR, absorption bands: 2820, 1740, 1610, 1440, 1130, 1070, 1000, 920 cm$^{-1}$.

NMR $^1$H (DMSO as the reference): 0.85 (s), 1.05 (t), 1.23(s), 3.16 (s), 3.43 (d), 3.63 (s), 4.15 (s), 4.40(s), 7.39(m), ppm.

Fraction 4 (DMSO as the reference)

NMR $^1$H: 0.8 (m), 1.05 (s), 1.24 (s), 1.51 (s), 3.41 (s), 3.65 (s), 4.30 (s), 4.41 (s), 7.46 (m), 8.40 (m), ppm Fraction 5 (DMSO as the reference)

IR, absorption bands: 2953, 1742, 1620, 1439, 1234, 1130, 1084, 900, 830 cm$^{-1}$.

NMR $^1$H: 1.03 (t), 1.47 (d), 3.16 (s), 3.40 (quadruplet), 3.63 (s), 4.22 (s), 4.26 (s), 4.39 (s), 7.45 (s), ppm.

A further object of the present invention relates to the process for extracting and isolating the previously characterised active ingredient, contained in the *Mimosa tenuiflora* cortex and having cellular regenerative activity.

The said process mainly consists in a successive extraction by means of solvents.

In a first step the *Mimosa tenuiflora* cortex was pulverised or ground, preferably by means of a blade mill, obtaining a grinding which was placed in a reactor in which a prior extraction had been carried out with chloroform in a ratio of from 2:1 to 8:5 p/v (parts by weight of grinding: parts in volume of chloroform). The mixture was heated at a temperature of from about 50° C. to 70° C., with the purpose of eliminating alkaloids, fats and other chemical compounds present in the cortex. The chloroform fraction was then separated, preferably by filtration, using a type of filter-press.

In a second step, once the chloroform phase had been separated, the mass obtained was subjected to another extraction with ethanol in a ratio of from 1:3 to 1:12 p/v, respectively, stirring it continuously at a temperature of from about 60° C. to 80° C. In this manner the active ingredient was obtained in an alcohol solution. It was then filtered and the ethanol was eliminated by distillation. The residue obtained was dried in a drier. This step may be repeated various times, collecting and gathering the ethanol extracts.

Then in a third step, the dry residue was subjected to a further extraction with water in a ratio of 1:2 p/v respectively, stirring it continously at a temperature of from about 50° C. to 100° C. In this manner an aqueous solution of the active ingredient was obtained which was separated by filtration. This extraction step with water may be repeated various times and the aqueous solutions obtained collected. The collected aqueous solutions were allowed to stand at ambient temperature for a period of from 12 to 92 hours. Then a prior concentration of the active ingredient was carried out by partial evaporation of the water. For such purpose, the aqueous solutions of active ingredient were refiltered and the water was partially evaporated until an approximate 20% solids concentration was obtained.

Finally, it was placed in a drier and dried. The active ingredient was obtained as an odourless powder having a reddish coffee colour and a bitter taste. The elemental analysis of the extracted active ingredient indicates that the proportion of C, H and O is the following:
C: 54–57%
H: 4.5–5.4%
O: 36.5–37.5%

The identification of this compound was carried out by ultraviolet/visible, infra-red and Nuclear Magnetic Resonance spectroscopy, obtaining spectra similar to those illustrated in FIGS. 1 to 4 of this application, the characteristics of which have already been mentioned.

In accordance with the preferred process, the active ingredient may be prepared with a yield ranging from about 9 to 11%, the purity of the so obtained product being suitable for pharmaceutical purposes.

Alternatively, the active ingredient may also be obtained by extraction with an ethanol-water mixture, in a ratio of 1:1 (v/v), followed by elimination of the ethanol by distillation and then carrying out a further extraction with chloroform on the aqueous solution in order to ensure purification. Then the aqueous solution resulting from the elimination of the chloroform, is dried to obtain the active ingredient in a powdered form having the previously mentioned characteristics.

The solvents cited in the previously mentioned extractions are not critical, although they are preferred. Nevertheless, other solvents such as methanol, acetone, ethyl acetate, ethyl ether, DMSO, hexane, benzene, carbon tetrachloride, tetrahydrofurane or petroleum ether may be used. Both the lixiviation-percolation as well as the maceration or continuous extraction method may be used as extracting techniques, or any other similar technique known to persons skilled in the art.

Another object of this invention is the preparation of compositions containing the active ingredient extracted from the *Mimosa tenuiflora* cortex having epidermal regenerative activity. These compositions are useful as cosmetics, in the therapy of burns and in the therapy of injuries of other kinds, such as ulcers, varicose veins, surgical wounds, slight injuries, cracks, chafings, grazes, sores and ezcemas.

These cosmetic and pharmaceutical compositions may adopt a solid or liquid form. In the solid form they may be powders, dustable powders, ointments, etc. In the liquid form they may be emulsions, suspensions, gels, shampoos, etc. The suspensions or emulsions may likewise be converted into aerosols.

The pharmaceutical compositions generally contain a quantity of active ingredient comprised between approximately 1 and 70% by weight, along with an adequate amount of suitable carriers and excipients.

The preferred pharmaceutical compositions are the aqueous solution and the dustable powder.

The dosage of the active ingredient depends upon the area of the lesion and its profundity. When applied typically on the injured zone it forms a film having a thickness of from 0.02 to 0.1 mm.

The comparative study of the edpidermal regenerative potentiality of the powdered Tepescohuite cortex and of its active ingredient, was carried out on 43 mice (*Rattus Norvergicus*) afflicted with second degree burns on 20% of their body surface. It was also evaluated on 80 human patients afflicted with second degree burns, superficial and deep, on 10 to 40% of their body surface.

A series of solutions were prepared with the powder of the active ingredient which presented a concentration range of from 5 to 60%. Therefore the advantages presented by the solution of active ingredient when compared with the powdered Tepescohuite cortex are the following:

The solution, at the time of application, presents the advantage that it molds and adheres totally to the wound without leaving uncovered spaces. It forms a protective layer which dries rapidly, permitting gaseous exchange.

Thus a drying action is carried out, it covers the nerve endings as well as the cellular layers of the skin which are also unprotected when the epidermis is injured, it prevents the entrance of microorganisms, it avoids the pyrogenic and algogenic activity produced by the powdered cortex, thereby preventing the presence of pruritus, since it eliminates the loss of liquids hydrostatic unbalance is reduced.

It maintains the acid pH of the traumatised skin, it presents a greater mobility of the extremities, it acts as as a potent granulation tissue inducer.

It presents a potent aniogenic action which favours arterial neoformation and vasodilatation and activates, as a chemotactic, the macrophagous population.

It is a potent collagenogenetic inducer on the part of the fibroplasts. It therefore reduces collagen fiber alignment in the direction of the traction lines and therefore the formation of hypertropic and keloid scars.

It induces regeneration of the skin more rapidly than in the case of the powdered cortex.

For quantification of the acute and sub-acute toxicity of the active ingredient of the invention, Albine mice (*Rattus Norvengicus*) and Wistar Lewis mice of both sexes, were used, having an average weight of 350 grams in the case of males and 275 grams in the case of females. The compound was tested subcutaneously.

In the acute toxicity study, the $LD_{50}$ value was not obtained in any of the tested doses (0.100, 177, 316, 562; 1000, 1778, 3162 mg/kg) since the maximum value of the index of the loss of life rate reached was of 10%, for an LD of 3162 mg/kg, with an observation time of 14 days, wherefore the average $LD_5$ value was of 650 mg/kg.

In the sub-acute toxicity study, the $LD_{50}$ value was obtained, which was of 9.759 g/kg with an observation time of 32 days. The $LD_5$ concentration value in this case fell to 520 mg/kg.

The histopathological study was carried out on the skin, kidney, liver, intestine and muscle, using the conventional techniques of fixing and tinting the tissue for H and E. Large deposits of an amorphous ochre material were found on the skin, presenting a strong granulamatous reaction of a foreign body type. A large number of macrophagous and fibroplasts and a high production of collagen were also seen.

This study led us to believe that the material presents a low absorption rate, wherefore the active ingredient may be considered as non-toxic, since concentrations of 585 would be necessary for a loss of life probability of 50% in an adult person weighing 60 kg, innoculating it subcutaneously.

Local application was used on a patient. In this case the toxicity was considerably reduced.

A clinical study of the active ingredient was carried out on 50 burned patients, who were subdivided into 4 groups in accordance with the extent of the afflicted area:
group I. Less than 10%
group II=From 11 to 20%
group III. From 21 to 30%
group IV. More than 31%.

In group I the blood pressure was evaluated on three occasions, the following values were observed in the Systolic Blood Pressure (MM Hg) x+S; 112.85+17.04; 117.5+17.08 and 117.5+20.6, respectively. Insofar as the diastolic Blood Pressure, the values were of $78\pm21.68$; $72.5\pm12.58$ and $76.66\pm15.27$. Both the systolic as well as the diastolic Blood Pressure values did not demonstrate important statistic differences.

Pulsation (frequency per minute): $87.43\pm13.34$; $88\pm8.07$; $90.25\pm7.93$ and $80.5\pm8.22$, similar values without important statistic differences.

Referring to the respiratory frequency (per minute), the following values were observed $25.7\pm7.16$; $23\pm3.74$; $22.75\pm2.5$ and $22.5\pm2.08$ also with no significant P.

The body temperature measured in the morning presented $36.57\pm0.62$; $36.75\pm0.98$; $36.55\pm1.02$ and $36.77\pm0.82$. The data corresponding to the afternoon was the following: $37.11\pm0.678$; $36.85\pm0.2$; $36.27\pm0.26$ and $36.68\pm0.7$, with important differences between the first day (high temperature) and the seventh day (lowest temperature) in $P<0.05$.

The hematic biometry showed:
Haemoglobin (Hb) g/dl $\bar{x}\pm S$; $13.58\pm1.39$ and $13.45\pm0.86$.
Hematocrit (Ht) % $\bar{x}\pm S$; $91.38\pm5.55$; $41.0\pm4.74$.
Leucocytes ($1\times10^3$ $MM^3$) $10936\pm3110$ and $8683\pm962$.

Neither were important differences observed in all of them, nor were there differences in the Urinary flow (ML/24 hours)$\bar{x}\pm S$; $705\pm327.14$; $836.66\pm433.11$; $785\pm513.71$ and $782.5\pm882.7$.

Upon analysing the serous secretion, haematic secretion, purulent secretion, pain, pruritus, fever, inflammation, infection, granulation and scarring symptoms, an improvement during the first week of observance and important differences as from the third day were observed and the serous secretion (P0.001), haematic secretion (P 0.05), pain (P 0.001), fever (P 0.001), inflammation (P 0.01), granulation (P 0.001) and scarring (P 0.01) symptoms were maintained at the end of the week, but not so in the case of purulent secretions and prutitus. Similar results were obtained with Groups II, III and IV.

From all this it is deduced that the active ingredient extracted from the *Mimosa tenuiflora* cortex has epidermal regenerative properties, it is non-toxic, it does not produce side effects, it reduces pain, fever, and secretions and it stimulates scarring. It therefore has a wide application in therapeutic purposes.

Some examples for extracting the active ingredient as well as for preparing the pharmaceutical compositions are given below merely by way of illustration and not limiting of the scope of the invention.

EXAMPLE 1

The Tepescohuite cortex was dried and ground in a blade mill. Fifty Kg. of this pulverized cortex were placed in a reactor having a sufficient capacity to which chloroform in a ratio of from 2:1 to 8:5 p/v respectively were added, stirring continuously at a temperature of from 50° to 80° C. for a period of from 4 to 8 hours. The chloroform was separated by filtration (using a filter press).

The pulverized cortex was extracted with ethanol in a ratio of from 1:3 to 1:12 p/v respectively, at a temperature of from 60° to 80° C., maintaining the stirring. It was filtered and the extraction with ethanol was repeated. The ethanol extracts were collected and the ethanol was eliminated by distillation. The residue was dried in a drier. The powder obtained was extracted with water in a ratio of from 1:2 to 1:10 p/v respectively at a temperature of from 50° to 100° C., maintaining the stirring.

The extraction was repeated with water and the aqueous solutions were collected, filtered and allowed to stand at ambient temperature for a period of from 12 to 92 hours.

It was refiltered and the aqueous solution was concentrated to a 20% solid content. It was dried in a drier until an odourless, reddish coloured powder having a bitter taste was obtained. In this manner a compound having the following elemental analysis was obtained:
C 54 to 57%
H 4.5 to 5.4%
O 36.5 to 37.5%
This compound was identified by UV/VIS, IR. NMR analysis.

EXAMPLE 2

Fifty Kgs. of the pulverized cortex were placed in a reactor having a sufficient volume. A mixture of water-ethanol 1:1 v/v was added thereto. The ratio of the alcohol solution to weight of tepescohuite cortex was of from 4:1 to 10:1, respectively. This mixture was heated at a temperature of from 60° to 95° C. for a period of from 3 to 12 hours, stirring continuously. The ethanol solution was separated by filtration (filter press).

The same procedure was repeated with the cortex. The water-ethanol extracts were collected and the ethanol was eliminated by distillation, allowing it to stand for a period of from 12 to 96 hours. It was filtered and the aqueous solution was extracted with chloroform, stirring vigorously to ensure purification.

The aqueous solution was concentrated to a 20% solid content. It was then dried in a drier.

EXAMPLE 3

The procedure of example 1 was repeated, but the chloroform was replaced by ethyl ether and the ethanol by methanol.

EXAMPLE 4

A pharmaceutical composition of the active ingredient was prepared in the form of an ointment having the following composition:

| OINTMENT | |
|---|---|
| Tepescohuite powder | 10 g |
| Cocoa butter | 10 g |
| Carnauba wax | 5 g |
| Vegetable olive oil | 20 g |
| Hydrogenated lanolin | 10 g |
| Tween-80 | 1 g |
| Span-80 | 1 g |
| Methyl p-hydroxybenzoate | 1 g |
| Distilled water q.s. for | 100 |

The cocoa butter, the olive oil, the carnauba wax, the hydrogenated lanolin along with the Tween-80 and Span-80 were melted slowly, close to 30° C., whilst stirring continuously (lipophilic phase).

The methyl p-hydroxybenzoate and the Tepescohuite extract were dissolved in hot distilled water, close to 60° C.

The hot aqueous solution was added to the lipophilic phase maintaining the temperature between 60° and 70° C., stirring continuously for 15 minutes and then, once completely homogenized, it was introduced into respective flasks.

EXAMPLE 5

A hydrogel of the active ingredient having the following composition was prepared:

| HYDROGEL | |
|---|---|
| Tepescohuite powder | 6 g |
| Carbopol ® 934 (carboxyvinyl polymer | 0.9 g |
| Triethanolamine | 1 g |
| methyl P-hydroxybenzoate | 0.1 g |
| Isopropanol | 32 g |
| Distilled water to | 100 g |

The methyl p-hydroxybenozate was dissolved in one part of distilled water. The Carbopol ® 934 swelled in the solution obtained and it was then neutralized with the triethanolamine. Once a suspension of the active substance with Isopropanol was obtained, the volume was adjusted to 1000 g with distilled water.

EXAMPLE 6

A gel of the active ingredient having the following composition was prepared:

| GEL | |
|---|---|
| Tepescohuite powder (20% aqueous solution) | 8 g |
| Carbowax 6000 (poly(ethyleneglycol)monoalkyl ether) | 15 g |
| Carbowax 300 (poly(ethyleneglycol)monoalkyl ether) | 30 g |
| Carbowax 400 (poly(ethyleneglycol)monoalkyl ether) | 27 g |
| Glycerol | 18 g |
| Brig$^{35}$ (poly(ethyleneglycol)lauryl ether) | 2 g |

The components were melted together, with the exception of the active substance to which the melted mass was added in small quantities under stirring and the composition was homogenized.

EXAMPLE 7

A dustable powder of the active ingredient having the following composition was prepared:

| DUSTABLE POWDER | |
|---|---|
| Tepescohuite powder | 14 g |
| Zinc stearate | 5 g |
| Zinc oxide | 4.5 g |
| Aerosil ® R-200 | 3.8 g |
| Talcum to | 100 g |

The components were thoroughly homogenized to obtain a powdered mixture.

EXAMPLE 8

A bar of lipstick containing the active ingredient and having the following composition was prepared:

| THEPESCOHUITE LIPSTICK BAR | |
|---|---|
| Centesimal composition | |
| Tepescohuite extract | 10 g |
| Cetyl alcohol | 5 g |
| Lumpy White beeswax | 12 g |
| lanolin | 2 g |
| vaseline oil | 10 g |
| Ethyl stearate | 8 g |
| Carnauba wax | 10 g |
| Benzoic acid | 0.5 g |
| Spand | 0.5 g |
| Technical vaseline oil | 32 g |
| Water q.s. to | 100 g |

The lanolin, the waxes, the ethyl stearate and the Spand, along with the vaseline oil, were melted at a temperature of about 80° C. The mass was stirred slowly for a period of 30 minutes (lipophilic phase).

The benzoic acid and the tepescohuite extract were dissolved in hot distilled water, close to 100° C.

The aqueous solution was then added to the lipophilic phase, stirring continuously for another 30 minutes and poured into previously prepared molds.

EXAMPLE 9

An aqueous solution of the active ingredient having the following composition was prepared:

| SOLUTION | |
|---|---|
| Tepescohuite active ingredient powder | 20 g |
| Distilled water | 80 g |

The powder of the active ingredient was dissolved in hot water at 70° C.

Having described the object of the present patent of invention, it is declared that the main features thereof are specified in the following.

We claim:

1. A process for producing a *Mimosa tenuiflora* cortex extract which exhibits the following properties:
   a) odorless, reddish coffee-colored powder having a bitter taste;
   b) soluble in ethanol, DMSO, methanol and acetone;
   c) insoluble in water, chloroform, ethyl acetate, ethyl ether, propanol, hexane, $CCl_4$, THF, dioxane, amyl alcohol, isopropyl alcohol, benzyl alcohol, and diethylamine;
   d) a melting point of about 222° C.;
   e) has the following Rf values in thin layer chromatography with the following eluting systems:

| Eluting System | Rf |
|---|---|
| Chloroform | 0 |
| ethyl acetate | 0 |
| petroleum ether | 0 |
| benzene | 0 |
| methanol-water-DMSO (1:1:1) v/v | 0.963 |
| ethanol-water-acetic acid (2:1:1) v/v | 0.817 |
| methanol-DMSO | 0.910 |
| DMSO | 1.000 |
| dioxane-methanol-ethyl acetate (1:1:1) v/v | 0 | f) contains no heavy elements;
   g) exhibits an ultraviolet absorption spectrum in ethanol solution, with absorption and absorbance maxima of 222 nm (a=2.840) and 281 nm (a=0.600);
   h) exhibits an IR absorption spectrum (in potassium bromide tablet) with main absorption bands at: 3290, 2910, 1630, 1530, 1450, 1190, 1150, 1110, 1020, 840, 620, 580 $cm^{-1}$;
   i) exhibits a proton NMR spectrum in $D_2O$ with signs at:
   1.13 (m), 3.36 (m), 4.33 (s), 5.1 (s), 6.24 (d), 8.01 (s), 8.81 (s), 9.01 (s), 9.98 (s), ppm;
   j) exhibits a $^{13}C$ NMR spectrum in $D_2O$ with signs at:
   17.5, 18.25, 18.75, 19.5, 20.02, 21, 23, 25, 25.5, 26.25, 27.5, 27.9, 32, 32.8, 33.56, 36.4, 36.52, 37.5, 42, 42.2, 43, 45.2, 47.2, 49.2, 50.2, 52.54, 55, 59.5, 60, 60.2, 62.7, 74.7, 65, 67.2, 68, 68.1, 69, 69.9, 70.5, 71.7, 74.2, 75.76, 76.5, 77, 78.2, 81.2, 82.5, 83, 89, 96, 98, 98.7, 100, 102, 103.2, 103.5, 105, 105.2, 105.5, 106.5, 107.5, 109.7, 112, 112.2, 112.5, 112.7, 115, 115.7, 117.5, 118.5, 119.7, 123.5, 127, 128, 128.8, 129, 130, 131.5, 132, 136.9, 137.5, 143, 144.2, 144.7, 144.5, 146.2, 149.5, 150.5, 151, 152.7, 153.5, 153.6, 153.7, 155.5, 156, 157, 158, 160, 164, 163, 166, 167 (only up to 170 was read);
   k) the elemental analysis is as follows:
   C: 54–57%
   H: 4.5–5.4%
   O: 36.5–37.5%
   which comprises subjecting ground *Mimosa tenuiflora* cortex to successive extractions with solvents by the steps of
   i) grinding the *Mimosa tenuiflora* cortex until a powder is obtained,
   ii) subjecting said powder to a first extraction with chloroform in a ratio of from 2:1 to 8:5 p/v respectively, at 50° to 70° C. and then filtering to remove chloroform and to obtain a residue,
   iii) subjecting said residue of step ii) to a second extraction with ethanol at a ratio of from 1:3 to 1:12 p/v respectively, at 60° to 80° C. and under continuous stirring, filtering and then distilling to eliminate said ethanol, in order to obtain a residue that is then dried, optionally repeating step iii),
   iv) subjecting said residue of step iii) to a third extraction with water at a ratio of from 1:2 to 1:10 p/v respectively, at a temperature of 50° to 100° C. under stirring, which step may be optionally repeated, collecting and separating the aqueous solutions by filtration and allowing them to stand for a period of from 12 to 92 hours, then
   v) concentrating the aqueous solution to a 20% solid content by elimination of water and then
   vi) drying the product of step v) to obtain the desired substance in a powdered form.

2. The process according to claim 1, wherein the extraction by solvents is carried out by lixiviation-percolation.

3. The process according to claim 1, wherein the extraction by solvents is carried out by maceration.

4. The process according to claim 1, wherein the extraction by solvents is carried out by continuous extraction.

* * * * *